(12) United States Patent
Liang et al.

(10) Patent No.: US 7,704,956 B2
(45) Date of Patent: *Apr. 27, 2010

(54) GLUTATHIONE-BASED DELIVERY SYSTEM

(75) Inventors: Hsiang Fa Liang, Taipei County (TW);
Yung Chu Chen, Taipei County (TW);
Ting Fan Yang, Taoyuan County (TW);
Li Wen Chang, Taoyuan County (TW);
Ae June Wang, Hsinchu (TW); Jui-Mei Lu, Hsinchu County (TW); Chi-Heng Jian, Yilan County (TW); Yi-Fong Lin, Taipei County (TW); Shin-Jr Liu, Kaohsiung County (TW)

(73) Assignee: Industrial Technology Research Institute, Hsinchu (TW)

( * ) Notice: Subject to any disclaimer, the term of this patent is extended or adjusted under 35 U.S.C. 154(b) by 54 days.

This patent is subject to a terminal disclaimer.

(21) Appl. No.: 12/000,261

(22) Filed: Dec. 11, 2007

(65) Prior Publication Data

US 2008/0095836 A1     Apr. 24, 2008

Related U.S. Application Data

(63) Continuation-in-part of application No. 11/303,934, filed on Dec. 19, 2005, now Pat. No. 7,446,096.

(51) Int. Cl.
*A61K 38/06* (2006.01)
*A61K 51/08* (2006.01)

(52) U.S. Cl. .................. 514/18; 424/1.21; 530/331; 977/773

(58) Field of Classification Search ............... None
See application file for complete search history.

(56) References Cited

U.S. PATENT DOCUMENTS

| | | | |
|---|---|---|---|
| 5,080,904 A | 1/1992 | Iga et al. | |
| 5,695,751 A | 12/1997 | Friedman et al. | |
| 6,627,732 B1 | 9/2003 | Sakon et al. | |
| 6,653,331 B2 | 11/2003 | Zhao et al. | |
| 7,446,096 B2 * | 11/2008 | Wang et al. | 514/18 |
| 2003/0109555 A1 | 6/2003 | Zhao et al. | |

FOREIGN PATENT DOCUMENTS

| | | |
|---|---|---|
| EP | 1 072 608 A1 | 1/2001 |
| JP | 63-2922 A | 1/1988 |
| WO | WO-99/54346 A1 | 10/1999 |
| WO | WO-00/28977 | 5/2000 |

OTHER PUBLICATIONS

[Retreived from] http://www.merriam-webster.com/dictionary/endogenous, 2 pages, 2009 [retreived on May 20, 2009].*
Kiwada, 1987, Chem. Pharm. Bull. 35, 2935-2942.*
Anuradha, 2004, Methods Find Exp Clin Pharmacol, 26, 5-8.*
Khan, 1981, Indian Journal of Biochemistry, 18, 440-441.*
Banks et al., Life Sciences, vol. 59, No. 23, 1996, pp. 1923-1943.
Zlokovic et al., Biochemical and Biophysical Research Communications, vol. 201, No. 1 May 30, 1994, pp. 402-408.
Kannan et al., The Journal of Biological Chemistry. vol. 271, No. 16, Apr. 19, 1996, pp. 9754-9758.
Kannan et al., Journal of Neurochemistry, vol. 73 No. 1, 1999, pp. 390-399.
Kannan et al., Elsevier Science B.V. 2000, pp. 374-382.
Zlokovic, Pharmaceutical Research, vol. 12, No. 10, 1995, pp. 1395-1406.
"Liposome carrier for liver disease treatment—contains N-higher acyl glutathione as base material", Derwent, XP002322756, abstract ( Jan. 7 1988).
Kiwada et al., Chemical and Pharmaceutical Bulletin, Pharmaceutical Society of Japan, Tokyo, JP., vol. 35, No. 7, pp. 2935-2942, XP002276804 Jul. 7, 1987.
Suntres et al., Journal of Pharmacy and Pharmacology, London, GB, vol. 46, No. 1, pp. 23-28 XP001105800 (Jan. 1, 1994).
Jurima-Romet et al., Journal of Pharmacy and Pharmacology, London, GB, vol. 43, No. 1, pp. 6-10 XP001105806 (1991).
Sugiyama et al., Journal of Controlled Release, Elsevier, Amsterdam, NL, vol. 62, No. 1-2, pp. 179-186, XP004363015 (Nov. 1, 1999).
Kabanov, et al., 1982, Institute of Physical Chemistry, Academy of Sciences USSR, Moscow, pp. 771-775.

* cited by examiner

*Primary Examiner*—Andrew D Kosar
*Assistant Examiner*—Satyanarayana R Gudibande
(74) *Attorney, Agent, or Firm*—Birch, Stewart, Kolasch & Birch, LLP

(57) ABSTRACT

A delivery system. The delivery system includes a carrier having a surface, an active compound comprising small molecule compounds or peptides for use as an analgesic encapsulated into the carrier, and a glutathione or a glutathione derivative grafted on the surface of the carrier. The invention also provides a method of analgesia including conducting the active compound to a subject.

24 Claims, 10 Drawing Sheets

GLUTATHIONE-BASED DELIVERY SYSTEM

This application is a Continuation-in-Part of U.S. patent application Ser. No. 11/303,934, filed Dec. 19, 2005, which issued as U.S. Pat. No. 7,446,096 B2 on Nov. 4, 2008, and entitled "GLUTATHIONE-BASED DELIVERY SYSTEM".

BACKGROUND OF THE INVENTION

1. Field of the Invention

The invention relates to a biological delivery system, and more specifically to a glutathione-based delivery system.

2. Description of the Related Art

The blood brain barrier (BBB) is composed of brain endothelial cells capable of blocking foreign substances, such as toxins, due to the tight junctions therebetween. Hydrophobic or low-molecular-weight molecules, however, can pass through the BBB via passive diffusion.

Nevertheless, active compounds, such as hydrophilic protein drugs for treating cerebral or nervous diseases and analgesic peptide drugs acting on the central nervous system, cannot enter brain tissue thereby due to large molecular weight or hydrophilicity, resulting in decomposition thereof by enzymes.

Current research has developed various methods of allowing active compounds to pass through the BBB, including structural modification to increase hydrophobicity of drugs, absorption-mediated transport (AMT) allowing positive-charged carriers to pass via charge absorption, carrier-mediated transcytosis (CMT) allowing hydrophilic metal ions such as $Na^+$ and $K^+$, di-peptides, tri-peptides or glucose to pass via transporters, and receptor-mediated transcytosis (RMT) allowing macro molecules such as insulin, transferrin, or low-density lipoprotein (LDL) to pass via transcytosis.

Glutathione (GSH) is an endogenous antioxidant. If concentration thereof in serum is insufficient, some nervous diseases, such as chronic fatigue syndrome (CFS), may occur.

In 1988, Kiwada Hiroshi provided a liposome capable of accumulation in liver comprising a N-acylglutathione such as N-palmitoylglutathione and a phospholipid such as phosphotidylcholine to target and treat liver diseases recited in JP63002922.

In 1994, Berislav V. Zlokovic asserted that glutathione (GSH) reaches and passes through the BBB of a guinea pig via a special route, such as GSH-transporter, without decomposition.

In 1995, Berislav V. Zlokovic asserted that glutathione (GSH) exists in brain, astrocyte and endothelial cells in millimolar concentration.

In 1995, Ram Kannan asserted that GSH uptake depends on $Na^+$ concentration. If $Na^+$ concentration is low, GSH uptake from brain endothelial cells may be inhibited. Hie also pointed Na-dependent GSH transporter located on the luminal side of the BBB manages GSH uptake and Na-independent GSH transporter located on the luminal side of the BBB manages efflux of GSH. Additionally, Kannan constructed a rat hepatic canalicular GSH transporter (RcGSHT) system using the brains of mice and guinea pigs to analyze cDNA fragments 5, 7, and 11. The results indicate that fragment 7 represents Na-dependent GSH transporter and fragments 5 and 11 represent Na-dependent GSH transporter.

In 1999, Ram Kannan built a mouse brain endothelial cell line (MBEC-4) model simulating BBB situation. The model proved that Na-dependent GSH transporter is located on the luminal side of the MBEC-4 cell.

In 2000, Ram Kannan asserted that GSH passes through the BBB via Na-dependent GSH transporter in human cerebrovascular endothelial cells (HCBC) and Na-dependent GSH transporter exists in the luminal plasma membrane of HCEC.

In 2003, Zhao Zhiyang provided an anti-cancer pro-drug bonded with glutathione s-transferase (GST)/glutathione (GSH) by sulfonamide covalent bonds to target and treat specific cancer cells after break of the sulfonamide bonds recited in US2003109555. This modification can protect amino groups of drugs, increase solubility thereof, and alter absorption and distribution thereof in body.

Additionally, various opioid-peptide secreted by cerebrum have been separated such as enkephalin, endomorphin-1, and endomorphin-2. These natural analgesics, acting on opioid receptors, have lower habituation and respiratory depression than morphine. However, such drugs cannot pass through the BBB due to low-stability in plasma. Delivery to the cerebrum can only be accomplished by intracerebroventricular injection or intrathecal injection.

Thus, administration of analgesic peptide drugs is desired preventing decomposition by enzymes and prolonging the analgesic effect thereof.

BRIEF SUMMARY OF THE INVENTION

The invention provides a delivery system comprising a carrier having a surface an active compound comprising small molecule compounds or peptides for use as an analgesic encapsulated into the carrier, and a glutathione (GSH) or a glutathione derivative grafted on the surface of the carrier.

The invention also provides a method of analgesia comprising conducting the active compound to a subject.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawing, wherein.

DETAILED DESCRIPTION OF THE INVENTION

Figure 1:
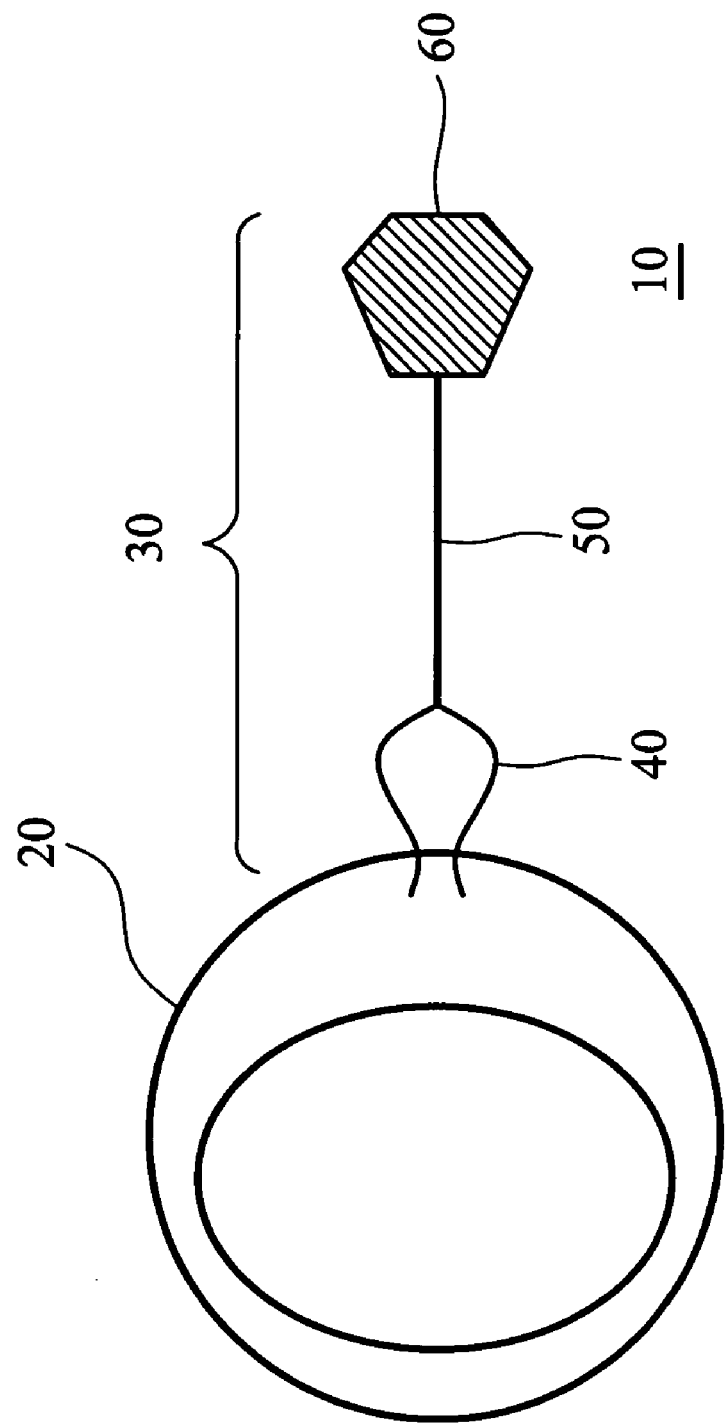
FIG. 1 shows a delivery system of the invention.

The following description is of the best-contemplated mode of carrying out the invention. This description is made for the purpose of illustrating the general principles of the invention and should not be taken in a limiting sense. The scope of the invention is best determined by reference to the appended claims.

The invention provides a delivery system comprising a carrier having a surface, an active compound comprising small molecule compounds or peptides for use as an analgesic encapsulated into the carrier, and a glutathione (GSH) or a glutathione derivative grafted on the surface of the carrier. The carrier may comprise nanoparticle, polymeric nanoparticle, solid liquid nanoparticle, polymeric micelle, liposome, microemulsion, or liquid-based nanoparticle. The liposome comprises at least one of lecithin such as soy lecithin and hydrogenated lecithin such as hydrogenated soy lecithin.

The liposome may further comprise cholesterol, water-soluble vitamin E, or octadecyl amine to increase serum resistance or charge amounts. The molar composition ratio of the liposome may be 0.5-100% of lecithin or hydrogenated lecithin, 0.005-75% of cholesterol or water-soluble vitamin E or 0.001-25% of octadecyl amine.

The carrier has an encapsulation efficiency of about 0.5-100%. The active compound may comprise small molecule compounds such as gabapentin, peptides such as enkephalin, proteins, DNA plasmids, oligonucleotides, or gene fragments and have a molar ratio of about 0.0005-50% in the carrier. Some of the small molecule compounds and the peptides may be used as an analgesic. The analgesic small molecule compounds may comprise morphine or gabapentin. The analgesic peptides may comprise endogenous opioid peptides such as endomorphin-1 or endomorphin-2.

The targeted carrier may target glutathione transporters of organs such as heart, lung, liver, kidney, or blood brain barrier.

Specifically, the active compound can pass through the blood-brain-barrier (BBB), such as brain endothelial cells, with the targeted carrier and has a cell penetration ratio of about 0.01-100%.

The invention provides a compound comprising a moiety comprising a vitamin E derivative or a phospholipid derivative, a polyethylene, glycol (PEG) or a polyethylene glycol derivative bonded thereto, and a glutathione (GSH) or a glutathione derivative bonded to the polyethylene glycol or the polyethylene-glycol derivative.

The vitamin E derivative comprises tocopherol derivatives or tocotrienol derivatives and may be α-tocopherol, β-tocopherol, γ-tocopherol, δ-tocopherol, α-tocotrienol, β-tocotrienol, γ-tocotrienol, δ-tocotrienol, α-tocopherol succinate, β-tocopherol succinate, γ-tocopherol succinate, δ-tocopherol succinate, α-tocotrienol succinate, β-tocotrienol succinate, γ-tocotrienol succinate, δ-tocotrienol succinate, α-tocopherol acetate, β-tocopherol acetate, γ-tocopherol acetate, δ-tocopherol acetate, α-tocotrienol acetate, β-tocotrienol acetate, γ-tocotrienol acetate, δ-tocotrienol acetate, α-tocopherol nicotinate, β-tocopherol nicotinate, γ-tocopherol nicotinate, δ-tocopherol nicotinate, α-tocotrienol nicotinate, β-tocotrienol, nicotinate, γ-tocotrienol nicotinate, δ-tocotrienol nicotiniate, α-tocopherol phosphate, β-tocopherol phosphate, γ-tocopherol phosphate, δ-tocopherol phosphate, α-tocotrienol phosphate, β-tocotrienol phosphate, γ-tocotrienol phosphate, or δ-tocotrienol phosphate.

The phospholipid derivative may have formulae comprising $$R_1 - A_1 - \quad \text{or} \quad (I)$$

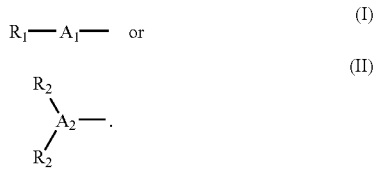

(II)

In formula (I), $A_1$ is sphingosine and $R_1$ may comprise octanoyl or palmitoyl. In formula (II), $A_2$ is phosphoethanoamine and $R_2$ may comprise myristoyl, palmitoyl, stearoyl, or oleoyl.

The polyethylene glycol (PEG) or the polyethylene glycol derivative has a polymerization number (n) of about 6-210. The molecular weight of the polyethylene glycol (PEG) or the polyethylene glycol derivative may be altered with various vitamin E derivatives or phospholipid derivatives. For example, when PEG or its derivative is bonded to vitamin E derivatives, it may have a molecular weight of about 300-10000, when PEG or its derivative is bonded to the phospholipid derivatives represented by formula (I), it may have a molecular weight of about 750-5,000', and when PEG or its derivative is bonded to the phospholipid derivatives represented by formula (II), it may have a molecular weight of about 350-5,000.

The polyethylene glycol derivative may comprise carboxylic acid, maleimide, PDP, amide, or biotin.

Referring to FIG. 1, the delivery system of an embodiment is illustrated. The delivery-system 10 comprises a liposome-20 and a ligand-30 grafted thereon. The ligand; 30 comprises a moiety 40 comprising a vitamin E derivative or a phospholipid derivative, a polyethylene glycol (PEG) or a polyethylene glycol derivative 50 bonded thereto, and a glutathione (GSH) or a glutathione derivative 60 bonded to the polyethylene glycol and the polyethylene glycol derivative.

Active compounds, such as proteins, peptides, or small molecule compounds, transported by the targeted carrier with a novel glutathione (GSH) ligand provided by the invention can effectively pass through blood-brain-barrier by carrier-mediated transcytosis (CMT) or receptor-mediated transcytosis (RMT) to treat cerebral or nervous diseases.

The invention also provides a method of analgesia comprising conducting the active compound to a subject.

The active compound may comprise small molecule compounds or peptides, for use as an analgesic. The analgesic small molecule compounds may comprise morphine or gabapentin. The analgesic peptides may comprise endogenous opioid peptides such as endomorphin-1 or endomorphin-2.

The active compound may further be grafted with a glutathione (GSH) or a glutathione derivative, or encapsulated by a carrier grafted with a glutathione (GSH) or a glutathione derivative. The carrier may comprise nanoparticle, polymeric nanoparticle, solid liquid nanoparticle, polymeric micelle, liposome, microemulsion, or liquid-based nanoparticle.

For pain treatment, the active compound grafted with the glutathione (GSH) or the glutathione derivative provides longer analgesic effect than the active compound without graft of the glutathione (GSH) or the glutathione derivative thereon. The active compound encapsulated by the carrier provides longer analgesic effect than the active compound without encapsulation by the carrier.

In an embodiment, the analgesic peptide drugs such as endomorphin-1 or endomorphin-2 pass through the BBB by, for example, intravenous injection, rather than by intracerebroventricular injection or intrathecal injection. Also, the retention time in plasma of such drugs grafted with glutathione (GSH) or encapsulated by carrier is prolonged, improving analgesic effect.

EXAMPLE 1

Preparation of TPGS-Glutathione

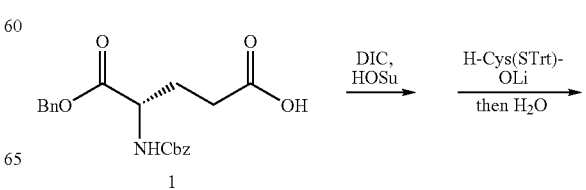

1

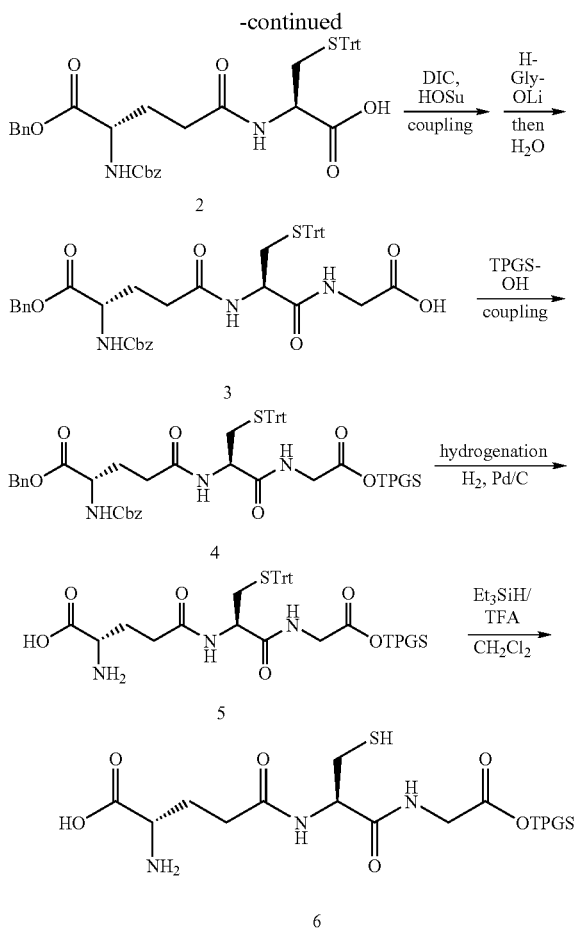

A stirred solution of N-Cbz Benzyl amino acid (N-Cbz Glutamine, 1.0 equiv) and N-hydroxysuccinimide (HOSu, 1.0 equiv) in 15 mL DME was cooled to 0° C. Dicyclohexylcarbodiimide (DIC, 1.0 equiv) was added and stirred at this temperature for 4 hr. The reaction mixture was allowed to stand for 2 hr in a refrigerator and then filtered.

As expected, the pure compound was obtained in excellent yield (98%) after filtration of the dicyclohexylurea (DCU) formed and evaporation of the solvent. The residue was triturated in $Et_2O$/hexanes, filtered out, and then dried in vacuo to afford a white solid.

The (+)-S-tritylcysteine lithium salt (H-Cys(STrt)-OLi, 1.0 equiv) and sodium carbonate ($Na_2CO_3$, 5.0 equiv) were dissolved in 15 mL water, and then acetonitrile ($CH_3CN$) was added followed by the intermediated product obtained in Step-2. The mixture was vigorously stirred at room temperature for 3-6 hr until the TLC analysis indicated the absence of intermediated product in Step-2. The solution was washed with water (2*100 mL) and the organic phase was dried with $Na_2SO_4$, filtered, and concentrated in vacuo to afford the compound 2.

A stirred solution of compound 2 and N-hydroxysuccinimide (HOSu; 1.0 equiv) in 15 mL DME was cooled to 0° C. Dicyclohexylcarbodiimide (DIC, 1.0 equiv) was added and stirred at this temperature for 4 hr. The reaction mixture was allowed to stand for 2 hr in a refrigerator and then filtered.

After the DCU and solvent was removed, the glycine lithium salt (H-Gly-OLi, 1.0 equiv) and sodium carbonate ($Na_2CO_3$, 5.0 equiv) were dissolved in 15 mL water, and then acetonitrile ($CH_3CN$) was added followed by the intermediated product obtained in Step-4. The mixture was vigorously stirred at room temperature for 3-6 hr until the TLC analysis indicated the absence of intermediated product in Step-4. The solution was washed with water (2*100 mL) and the organic phase was dried with $Na_2SO_4$, filtered, and concentrated in vacuo to afford the compound 3.

The d-alpha tocopheryl polyethylene glycol 1000 succinate (TPGS-OH) was coupled with compound 3 via esterification to afford compound 4.

The compound 4 in 100 mL methanol was added 10% Pd—C (0.2 times the weight of protected tripeptide-TPGS). The suspension was stirred at room temperature for 16 hr under a balloon-filled with hydrogen. The suspension was filtered through Celite and evaporated, and the residue was crystallized from ethanol. Compound 5 was obtained.

Triethylsilane ($Et_3SiH$) and TFA-mediated deprotection of compound 5 in the presence of $CH_2Cl_2$ provided the compound 6 (that is GSH-TPGS).

Preparation of Met-Enkephalin Carrier Solution 0.5 g lipid containing 83.2% soybean phosphatidylcholine (SPC), 4.2% α-tocopherol succinate PEG 1500 (TPGS); 4.2% glutathione-TPGS (GSH-TPGS), and 8.4% cholesterol was placed in a 12.5 mL $ZrO_2$ mortar. Appropriate amounts of met-enkephalin were dissolved in 10 mM phosphate solution with pH7.4 to form a 4% drug solution. 0.5 mL drug solution and five $ZrO_2$ beads (10 mm of diameter) were then added to the mortar and ground with 500 rpm for one hour to form a sticky paste. Next, 0.2 g sticky paste and 1.8 mL phosphate solution (10 mM, pH7.4) were added to a 10 mL flask to hydrate under room temperature for one hour to form a carrier solution containing liposomes encapsulating met-enkephalin. The concentration of met-enkephalin in a liposome was 0.56 mg/mL. The encapsulation efficiency thereof was 33.3%. The mean diameter of the carrier was 173.1 nm as well as the polydispersity index (PI) was 0.243.

EXAMPLES 2-6

Preparation methods of Examples 2-6 are similar to Example 1. The distinctions therebetween are the various carrier compositions, as shown in Tables 1 and 2.

TABLE 1

| Examples | Soy lecithin | H-soy lecithin | Cholesterol | TPGS | TPGS-GSH | Octadecyl amine | Met-enkephalin |
| --- | --- | --- | --- | --- | --- | --- | --- |
| 2 | 10 | — | 1 | — | 1 | — | 0.48 |
| 3 | 10 | — | 1 | — | 1 | 1 | 1.60 |
| 4 | 9 | 1 | 1 | 0.5 | 0.5 | — | 1.60 |
| 5 | 9 | 1 | 1 | 0.75 | 0.25 | — | 1.60 |
| 6 | 9 | 1 | 1 | — | 1 | — | 1.60 |

TABLE 2

| Examples | Mean diameter (nm) | PI | Met-enkephalin concentration (mg/mL) | Encapsulation efficiency (%) |
|---|---|---|---|---|
| 2 | 162.7 | 0.227 | 0.56 | 31.70 |
| 3 | 161.4 | 0.046 | 4.00 | 70.33 |
| 4 | 214.1 | 0.003 | 3.25 | 68.85 |
| 5 | 165.3 | 0.137 | 3.40 | 68.48 |
| 6 | 214.5 | 0.116 | 3.99 | 80.78 |

EXAMPLE 7

Preparation of Gabapentin Carrier Solution 0.5 g lipid containing 83.2% soybean phosphatidylcholine (SPC), 4.2% α-tocopherol succinate PEG 1500 (TPGS), 4.2% glutathione-TPGS (GSH-TPGS), and 8.4% cholesterol was placed in a 12.5 mL $ZrO_2$ mortar. Appropriate amounts of gabapentin were dissolved in 10 mM phosphate solution with pH7.4 to form a 10% drug solution. 0.5 mL drug solution and five $ZrO_2$ beads (10 mm of diameter) were then added to the mortar and ground with 500 rpm for one hour to form a sticky paste. Next, 0.2 g sticky paste and 1.8 mL phosphate solution (10 mM, pH7.4) were added to a 10 mL flask to hydrate under room temperature for one hour to form a carrier solution containing liposomes encapsulating gabapentin. The concentration of gabapentin in a liposome was 1.08 mg/mL. The encapsulation efficiency thereof was 35.7%. The mean diameter of the carrier was 147.7 nm as well as the polydispersity index (PI) was 0.157.

COMPARATIVE EXAMPLE 1

Preparation of Met-Enkephalin Carrier Solution 0.5 g lipid containing 83.2% soybean phosphatidylcholine (SPC), 8.4% α-tocopherol succinate PEG 1500 (TPGS), and 8.4% cholesterol was placed in a 12.5 mL $ZrO_2$ mortar. Appropriate amounts of met-enkephalin were dissolved in 10 mM phosphate solution with pH7.4 to form a 4% drug solution. 0.5 mL drug solution and five $ZrO_2$ beads (10 mm of diameter) were then added to the mortar and ground at 500 rpm for one hour to form a sticky paste. Next, 0.2 g sticky paste and 1.8 mL phosphate solution (10 mM, pH7.4) were added to a 10 mL flask to hydrate under room temperature for one hour to form a carrier solution containing liposomes encapsulating met-enkephalin. The concentration of met-enkephalin in a liposome was 0.57 mg/mL. The encapsulation efficiency thereof was 31.1%. The mean diameter of the carrier was 164.1 nm as well as the polydispersity index (PI) was 0.281.

COMPARATIVE EXAMPLES 2-3

Preparation methods of Comparative Examples 2-3 are similar to Comparative Example 1. The distinctions therebetween are the various carrier compositions, as shown in Tables 3 and 4.

TABLE 3

| Comparative Examples | Soy lecithin | H-soy lecithin | Cholesterol | TPGS | Octadecyl amine | Met-enkephalin |
|---|---|---|---|---|---|---|
| 2 | 10 | — | 1 | 1 | 1 | 1.60 |
| 3 | 9 | 1 | 1 | 1 | — | 1.60 |

TABLE 4

| Comparative Examples | Mean diameter (nm) | PI | Met-enkephalin concentration (mg/ml) | Encapsulation efficiency (%) |
|---|---|---|---|---|
| 2 | 159.7 | 0.103 | 3.58 | 70.17 |
| 3 | 149.0 | 0.168 | 3.22 | 69.67 |

COMPARATIVE EXAMPLE 4

Preparation of Gabapentin Carrier Solution 0.5 g lipid containing 83.2% soybean phosphatidylcholine (SPC), 8.4% α-tocopherol succinate PEG 1500 (TPGS), and 8.4% cholesterol was placed in a 12.5 mL $ZrO_2$ mortar. Appropriate amounts of gabapentin were dissolved in 10 mM phosphate solution with pH7.4 to form a 10% drug solution. 0.5 mL drug solution and five $ZrO_2$ beads (10 mm of diameter) were then added to the mortar and ground at 500 rpm for one hour to form a sticky paste. Next, 0.2 g sticky paste and 1.8 mL phosphate solution (10 mM, pH7.4) were added to a 10 mL flask to hydrate under room temperature for one hour to form a carrier solution containing liposomes encapsilating gabapentin. The concentration of gabapentin in a liposome was 1.17 mg/mL. The encapsulation efficiency thereof was 38.5%. The mean diameter of the carrier was 155.8 nm as well as the polydispersity-index (PI) was 0.186.

EXAMPLE 8

In vitro penetration ratio test 1 of met-enkephalin liposome
The penetration ratio of met-enkephalin was measured using a RBE4/glioma cell model simulating BBB situations. The test results of Examples 1-2 (with glutathione) and Comparative Example 1 (without glutathione) are compared in Table 5.

TABLE 5

| Examples | Drug dose (μg) | Penetration ratio (%) | SD |
|---|---|---|---|
| Comparative Example 1 | 182.6 | 3.4 | 0.6 |
| Example 1 | 167.7 | 9.8 | 1.3 |
| Example 2 | 165.2 | 9.8 | 1.2 |

The results indicate that Examples 1 and 2 have an apparently higher penetration ratio (9.8%) of about 2.82 times greater than comparative example 1(3.4%).

EXAMPLE 9

In vitro penetration ratio test 2 of met-enkephalin liposome
The penetration ratio of met-enkephalin was measured using a RBE4/glioma cell model simulating BBB situations. The test results of Example 3 (with glutathione) and Comparative Example 2 (without glutathione) are compared in Table 6.

TABLE 6

| Examples | Drug dose (μg) | Penetration ratio (%) | SD |
|---|---|---|---|
| Comparative Example 2 | 250.0 | 3.55 | 0.36 |
| Example 3 | 250.0 | 6.99 | 1.43 |
| Example 3 (glutathione added) | 250.0 | 0.25 | 0.03 |

The results indicate that Example 3 has an apparently higher penetration ratio (6.99%) of about 1.96 times that of Comparative Example 2 (3.55%). Additionally, if cells were cultured with glutathione for 30 min before Example 3 was performed, the penetration ratio thereof was lowered by 0.25% due to the addition of glutathione which occupied the glutathione transporter of the cells to block binding of carriers, reducing drug penetration through the BBB. The result proves that the glutathione carrier provided by the invention passes through the BBB via glutathione ligand/transporter binding to induce carrier-mediated transcytosis (CMT) or receptor-mediated transcytosis (RMT).

EXAMPLE 10

Hot-Plate Test of Met-Enkephalin Liposome

Figure 2:
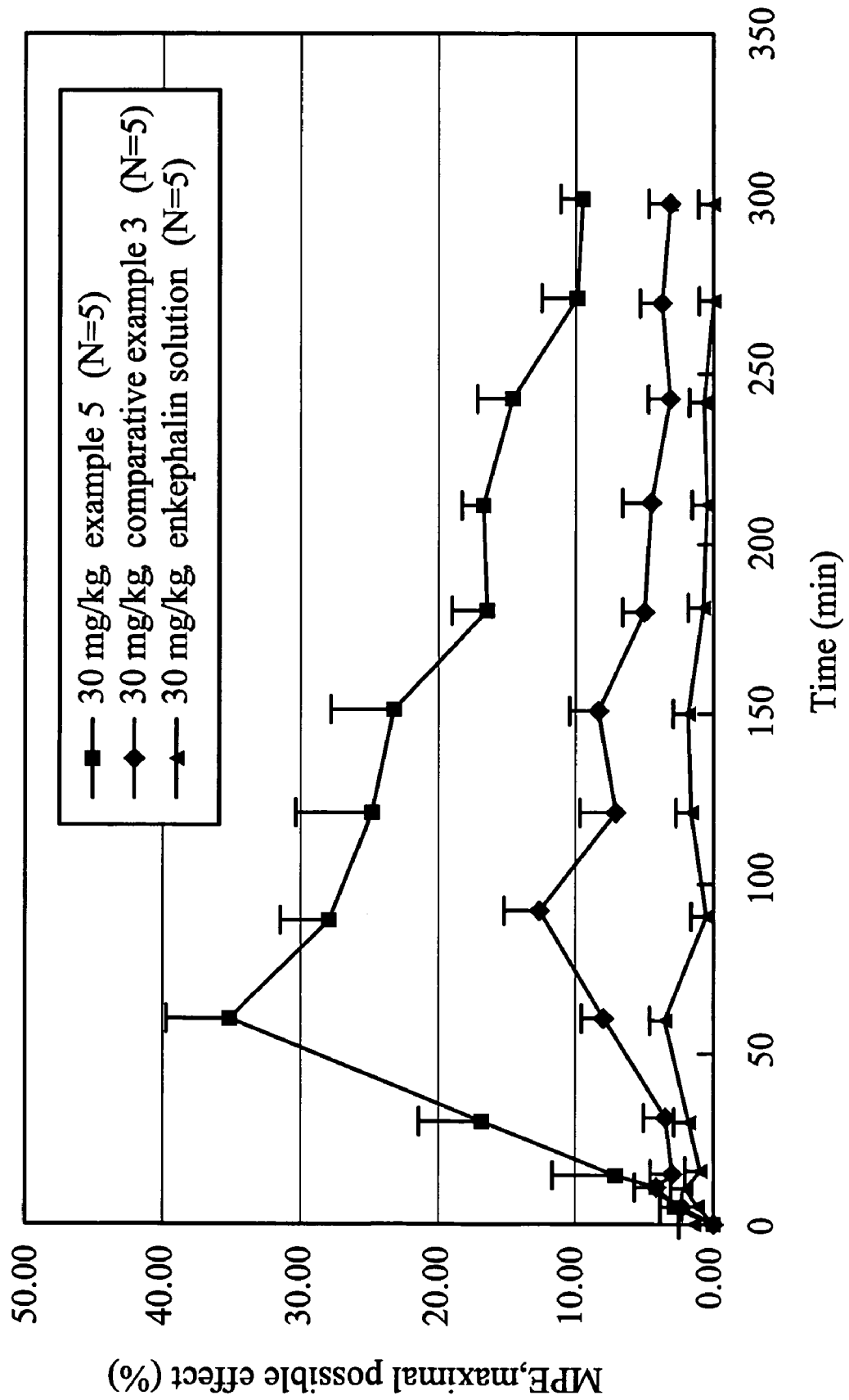
FIG. 2 shows the maximal possible effect (MPE) of various met-enkephalin carriers of the invention.
Figure 3:
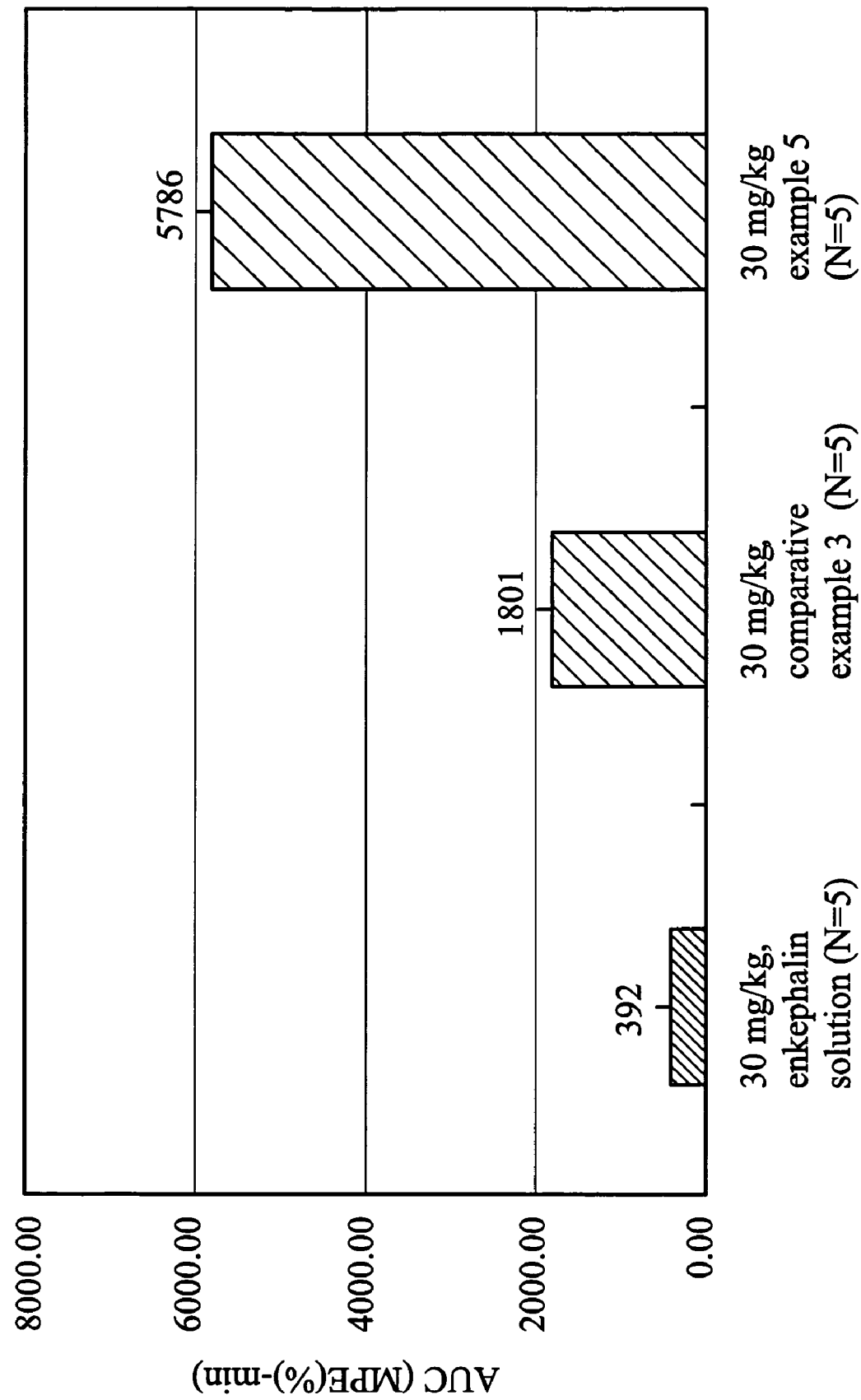
FIG. 3 shows the area under curve (AUC) of various met-enkephalin carriers of the invention.

After intravenous injection of a drug to a laboratory mouse, the mouse, was put on a 55° C. hot plate to evaluate the analgesic-effect on heat-induced pain. Referring to FIG. 2, for carriers without glutathione (Comparative Example 3), 90 min after injection, the maximal possible effect (MPE) of a 30 mg/mL dose was 13%. For carriers with glutathione (Example 5), 60 min after injection, the maximal possible effect (MPE) of 30 mg/mL dose was 37%. Referring to FIG. 3, according to the area under curve (AUC), Example 5 provides 3.2 times the analgesic effect of Comparative Example 3 and 14.7 times the met-enkephalin solution. Thus, drugs can be safely carried by the carrier with glutathione ligand to pass through the BBB to achieve analgesic effect.

EXAMPLE 11

Hot-Plate Test of Gabapentin Liposome

Figure 4:
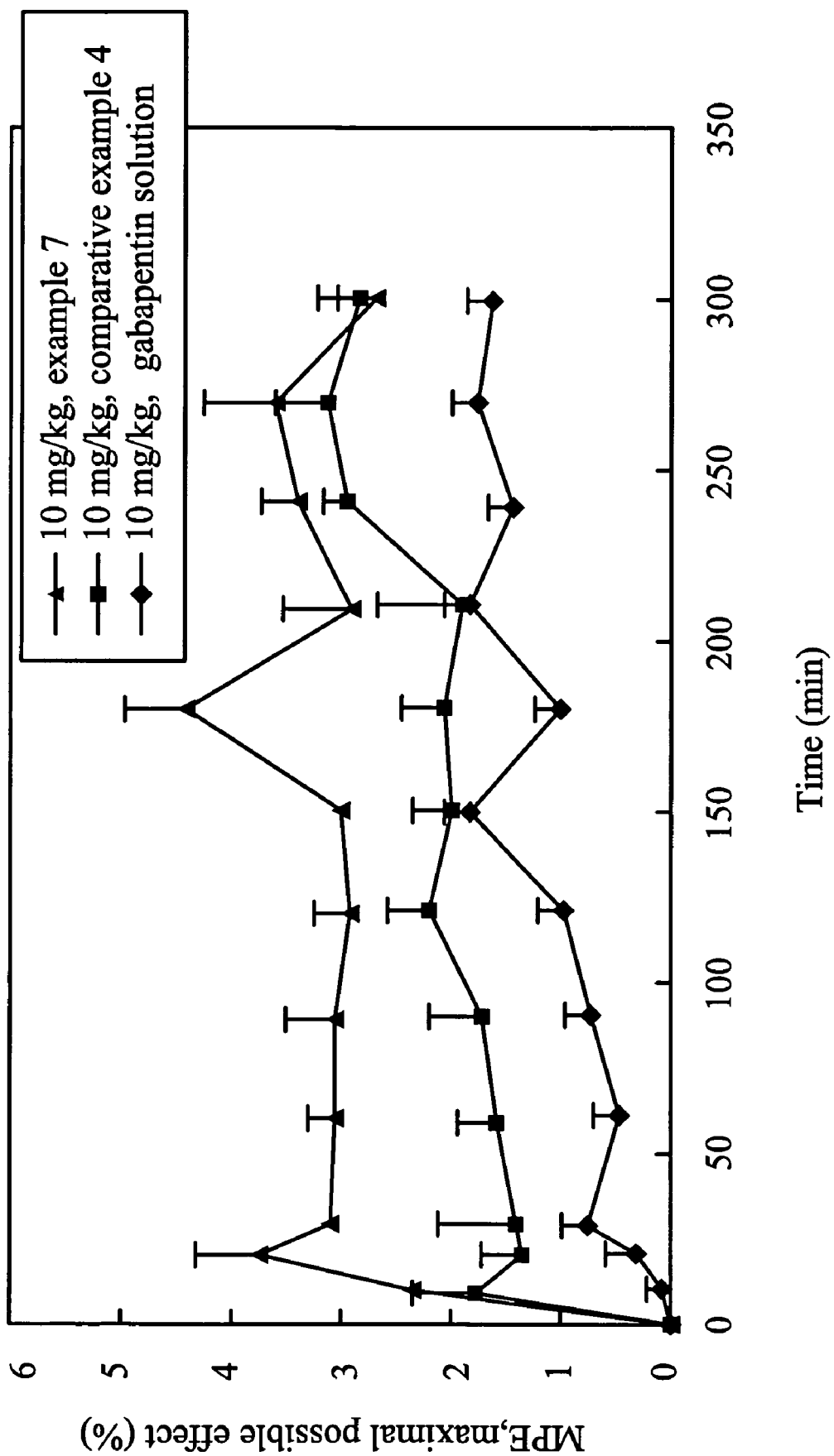
FIG. 4 shows the maximal possible effect (MPE) of various gabapentin carriers of the invention.
Figure 5:
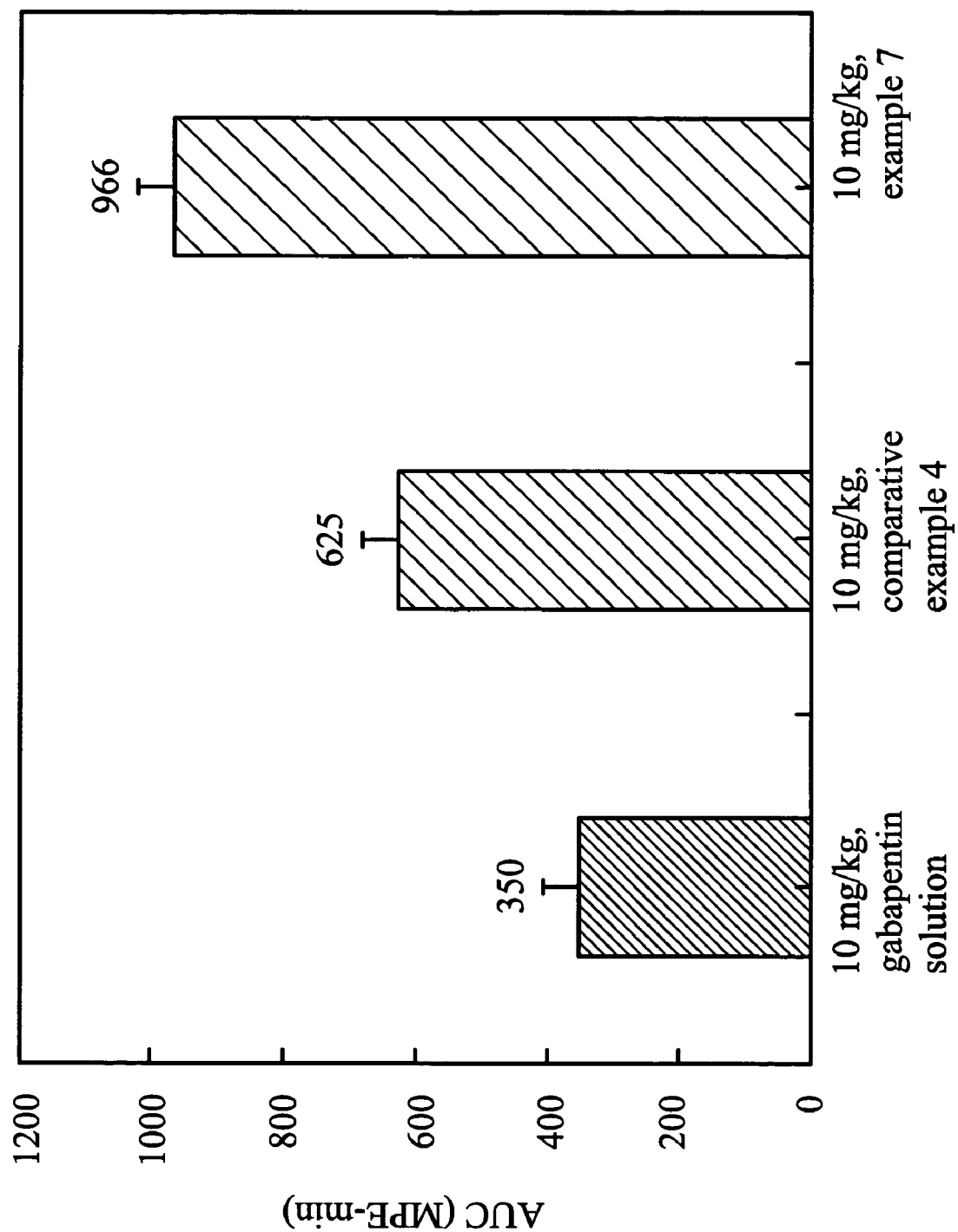
FIG. 5 shows the area under curve (AUC) of various gabapentin carriers of the invention.

After intravenous injection of a drug to a laboratory mouse, the mouse was put on a 55° C. hot plate to evaluate the analgesic effect on heat-induced pain. Referring to FIG. 4, for carriers without glutathione (Comparative Example 4), 270 min after injection, the maximal possible effect (MPE) of a 10 mg/mL dose was 3.15%. For carriers with glutathione (Example 7), 180 min after injection, the maximal possible effect (MPE) of a 10 mg/mL dose was 4.47%. Referring to FIG. 5, according to the area under curve (AUC), Example 7 provides 1.54 times the analgesic effect of Comparative Example 4 ($p<0.005$) and 2.76 times the gabapentin solution ($p<0.0005$). Thus, drugs can be safely carried by the carrier with glutathione ligand to pass through the BBB to achieve analgesic effect.

EXAMPLE 12

Serum Stability Test of Met-Enkephalin Liposome

Figure 6:
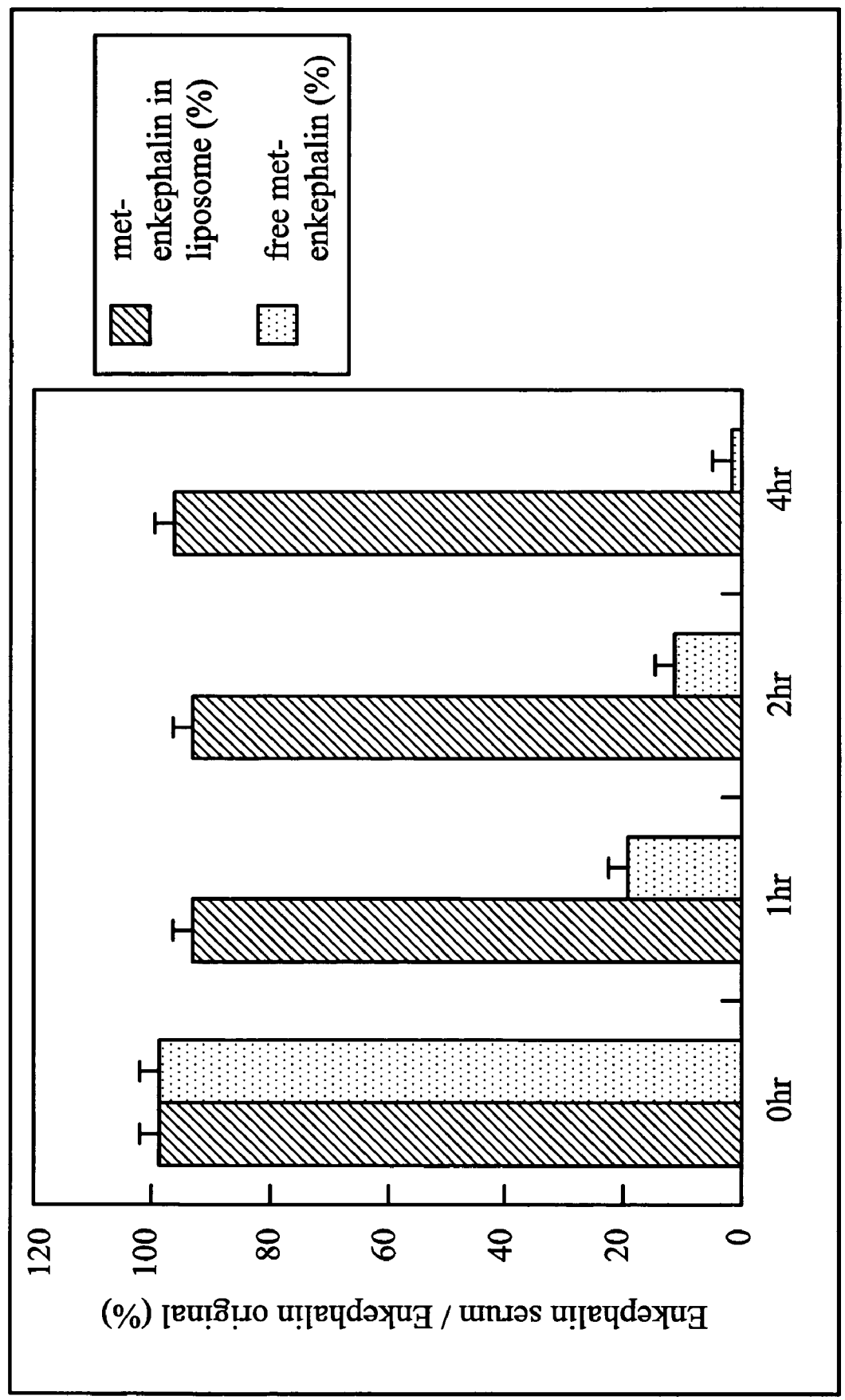
FIG. 6 shows serum stability of, free met-enkephalin and met-enkephalin in liposomes.

The 2 carriers provided by Example 5 and fetal bovine serum (FBS) were mixed with 1:1 (v/v) to form a solution. After being placed in a 37° C. water bath for 0, 1, 2, and 4 hours, respectively, the solution was analyzed by gel filtration (Sephrox CL-4B, 75 mm×120 mm) and measured residual concentration of met-enkephalin in liposomes. The results are shown in FIG. 6.

The results indicate that the concentration of met-enkephalin in liposomes, remains 93% above. However, residual concentration of free met-enkephalin decreases to 2%. It is clear that the carrier provided by the invention has high serum resistance.

EXAMPLES 13-17

Preparation of Endomorphin-1 Liposome 0.6 g lipid and 10 mg endomorphin-1 were placed in a 12.5 mL $ZrO_2$ mortar. The molar ratios of soybean phosphatidylcholine (SPC), α-tocopherol succinate PEG 1000 (TPGS), glutathione-TPGS (GSH-TPGS), and cholesterol in lipid were shown in Tables 7 and 8. Phosphate solution with pH7.4, 0.12 mL ethanol, and five $ZrO_2$ beads (10 mm of diameter) were then added to the mortar and ground with 500 rpm for one hour to form a sticky paste. Next, 0.2 g sticky paste and 0.6 mL phosphate solution (10 mM, pH7.4) were added to a 5 mL flask to hydrate under room temperature for one hour to form a liposome encapsulating endomorphin-1. The concentration of endomorphin-1 in the liposome was 1.6-1.8 mg/mL.

TABLE 7

| Examples | Soy lecithin | H-soy lecithin | DPPG | Cholesterol | Brij 76 | TPGS | TPGS-GSH | Endomorphin-1 |
|---|---|---|---|---|---|---|---|---|
| 13 | 10 | 1 | — | 1 | 2 | — | — | 0.32 |
| 14 | 10 | 1 | 1 | 1 | 2 | 1 | — | 0.32 |
| 15 | 10 | 1 | — | 1 | 2 | — | 0.25 | 0.32 |
| 16 | 10 | 1 | — | 1 | 2 | — | 0.5 | 0.32 |
| 17 | 10 | 1 | 1 | 1 | 2 | 0.5 | 0.5 | 0.32 |

TABLE 8

| Examples | Hydration ratio | Mean diameter (nm) | PI | Endomorphin-1 concentration (mg/mL) | Encapsulation efficiency (%) |
|---|---|---|---|---|---|
| 13 | 1/3 | 143.7 | 0.06 | 1.83 | 68.06 |
| 14 | 1/3 | 146.1 | 0.11 | 1.66 | 77.05 |
| 15 | 1/3 | 147.5 | 0.03 | 1.72 | 62.44 |
| 16 | 1/3 | 152.3 | 0.01 | 1.65 | 66.31 |
| 17 | 1/3 | 144.9 | 0.12 | 1.97 | 88.33 |

EXAMPLE 18

Hot-Plate Test of Endomorphin-1 Liposome

Figure 7:
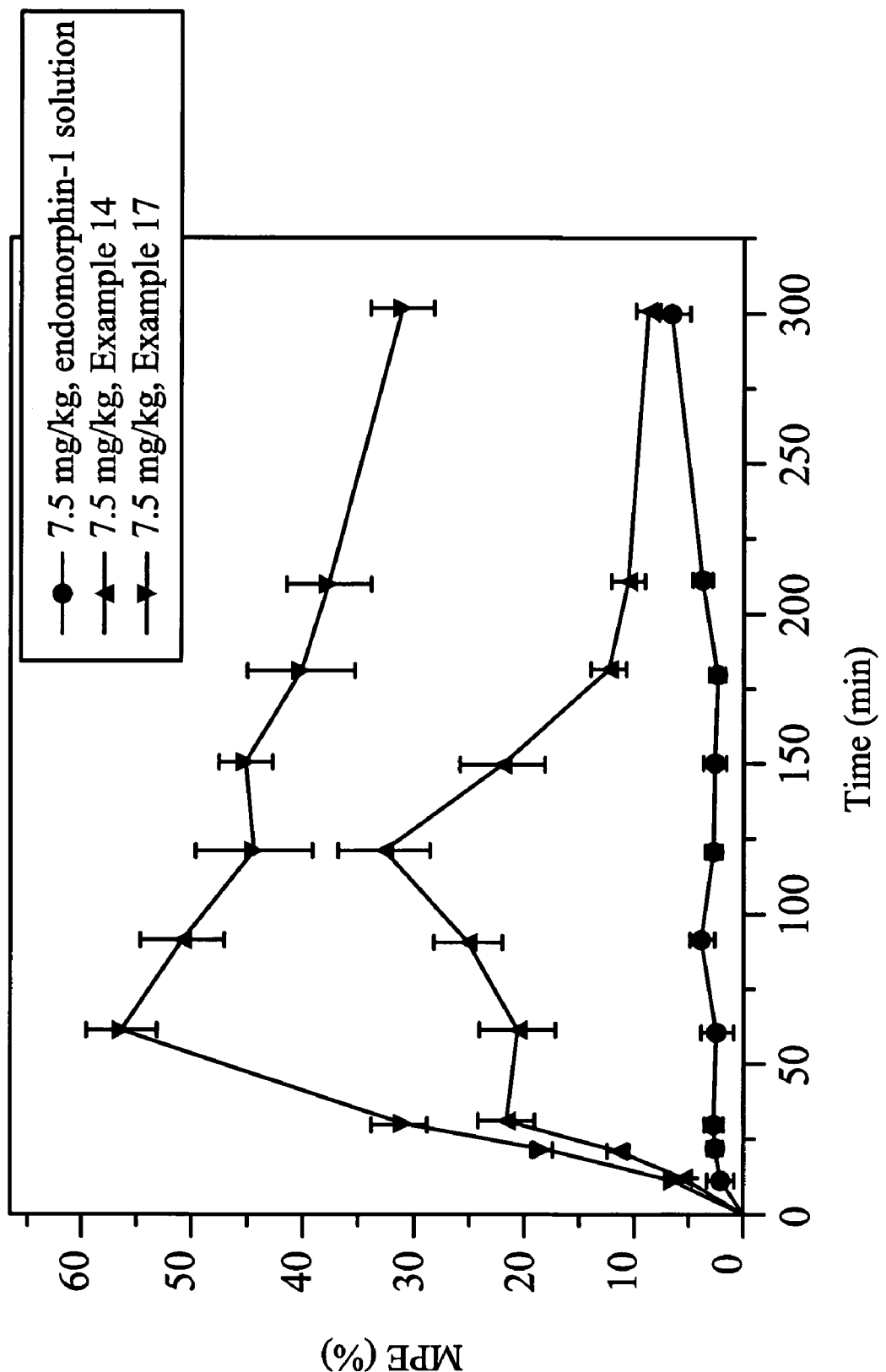
FIG. 7 shows the maximal possible effect (MPE) of various endomorphin-1 carriers of the invention.

After intravenous injection of a drug to a laboratory mouse, the mouse was put on a 55° C. hot plate to evaluate the analgesic effect on heat-induced pain. Referring to FIG. 7, for 7.5 mg/kg endomorphin-1 solution, no analgesic effect occurred. For endomorphin-1 liposomes without glutathione (Example 14), 120 min after injection, the maximal possible effect (MPE) of a 7.5 mg/kg dose was 33%. For endomorphin-1 liposomes with glutathione (Example 17), 60 min after injection, the maximal possible effect (MPE) of a 7.5 mg/kg dose was 57%. Even 5 hours later, Example 17 still remained 30% analgesic effect. The results indicate that more liposomes and endomorphin-1 were taken into brain through the liposomes with GSH ligands capable of targeting the BBB of Example 17. Until the liposomes were collapsed, endomorphin-1 was then slowly released, achieving a long analgesic effect. According to the area under curve (AUC), Example 17 provides 2 times the analgesic effect of Example 14 and 7 times the endomorphin-1 solution. Thus, the drug carrier modified by the glutathione ligand can effectively relieve the heat-induced pain.

EXAMPLE 19

Formalin Test of Endomorphin-1 Liposome

Figure 8:
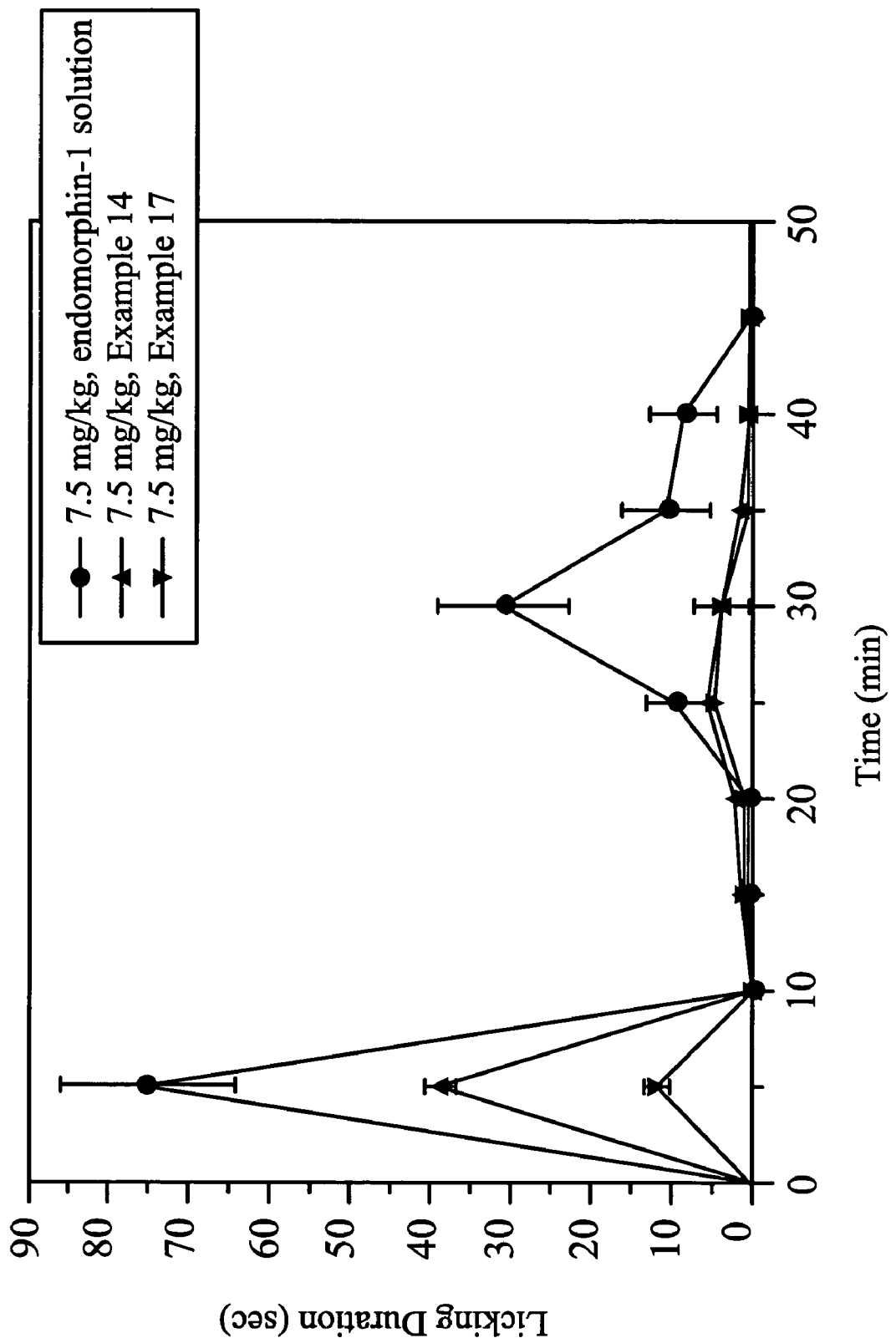
FIG. 8 shows the licking duration of various endomorphin-1 carriers of the invention.

After injection of formalin to a laboratory mouse's thenar, the mouse was intravenously injected by a drug to evaluate the analgesic effect on formalin-induced inflammatory pain. 1% formalin was injected to the mouse's right thenar. The mouse was then intravenously injected by the drug and the licking duration was measured. If the total licking duration was short, the analgesic effect of the drug was good. This animal model exhibited an early-phase pain induced by the central nervous system and a late-phase pain induced by the central nervous system and the peripheral nervous system. Suppression of the early-phase pain means that the drug has an analgesic effect on the central nervous system. Referring to FIG. 8, for 7.5 mg/kg endomorphin-1 solution, no analgesic effect occurred. The endomorphin-1 liposomes of Examples 14 and 17 shortened the licking duration. Specially, Example 17 with glutathione provides 4 times the analgesic effect of Example 14 without glutathione and 7 times the endomorphin-1 solution.

EXAMPLE 20

Neuropathic Pain Study

Figure 9:
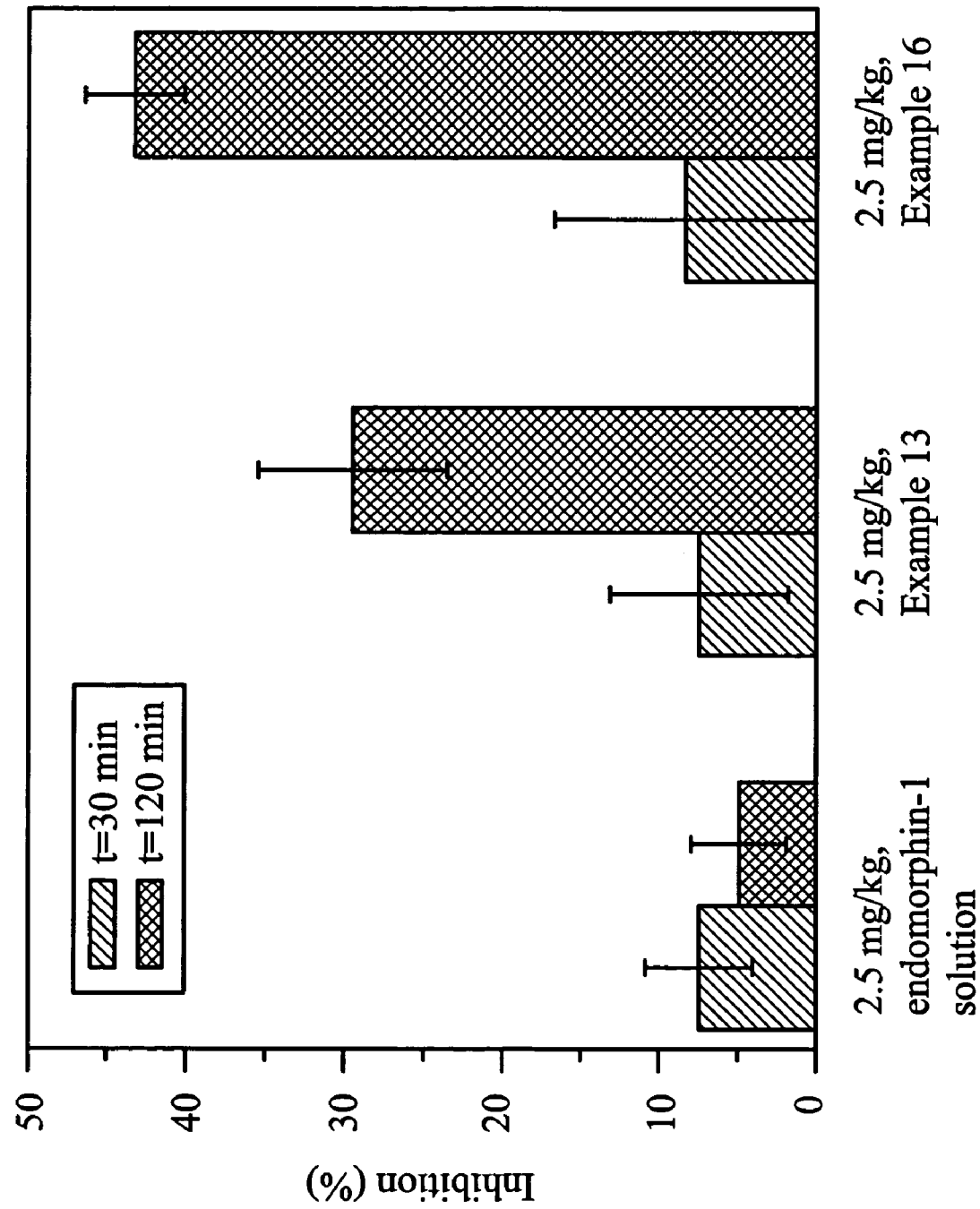
FIG. 9 shows the neuropathic pain inhibition of various endomorphin-1 carriers of the invention.

The sciatic nerve of a male wistar mouse was ligated to build a neuropathic pain animal model. 30 and 120 min after injection of a 2.5 mg/kg dose, the stress forcing the mouse's thenar to shrink was measured to evaluate the analgesic effect on the neuropathic pain. Referring to FIG. 9, after 30 min, for endomorphin-1 solution, Example 13 and Example 16, no apparent analgesic effect occurred. However, after 120 min, Example 16 with glutathione provides 1.5 times the analgesic effect of Example 13 without glutathione and 9 times the endomorphin-1 solution.

EXAMPLE 21

Pharmacokinetics of Endomorphin-1 Liposome

Figure 10:
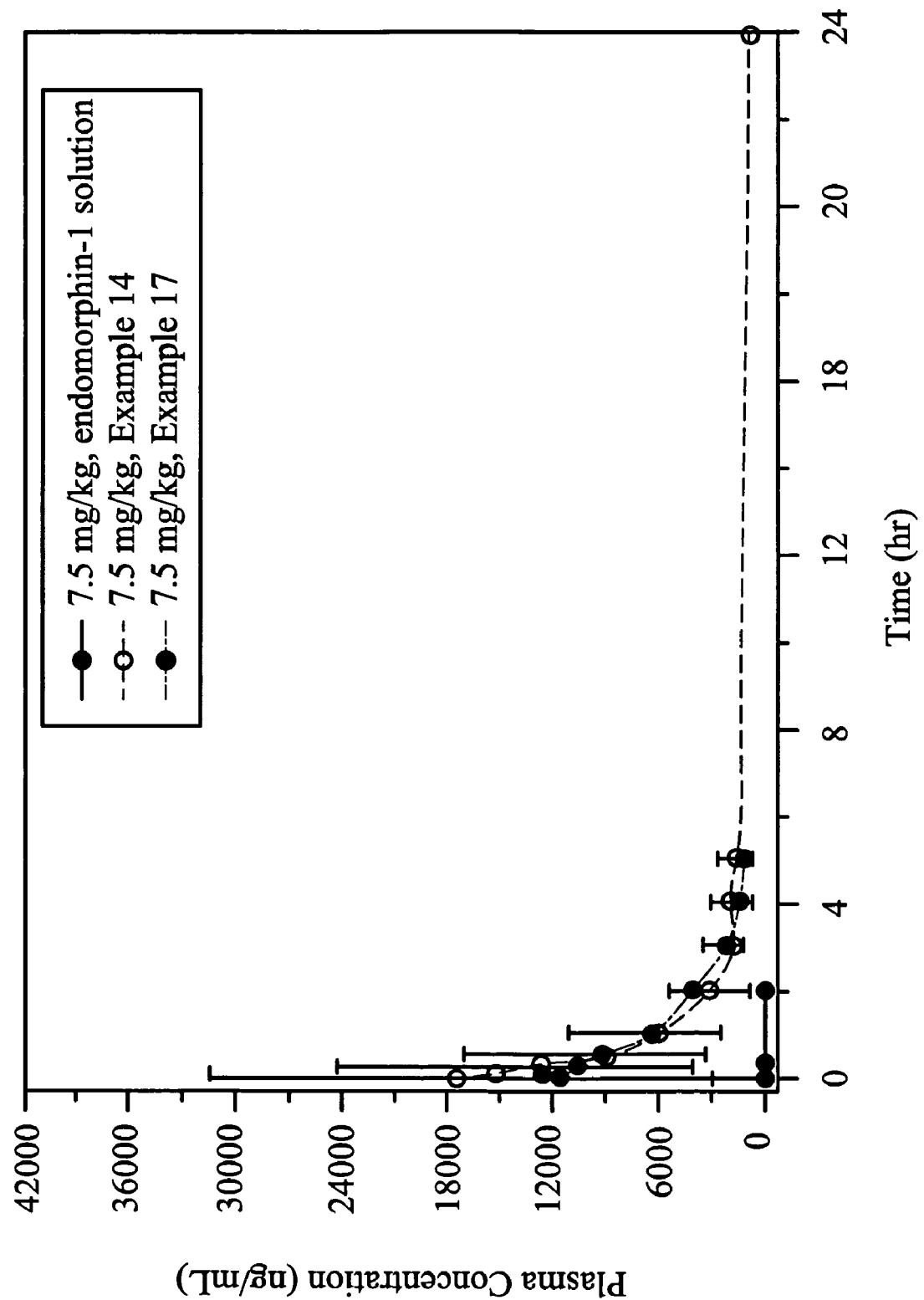
FIG. 10 shows the pharmacokinetics of various endomorphin-1 carriers of the invention.

The plasma concentration of endomorphin-1 of a wistar mouse was analyzed by LC-MS/MS to study the pharmacokinetics of the endomorphin-1 liposome. Referring to FIG. 10, for 7.5 mg/kg endomorphin-1 solution, no endomorphin-1 was detected merely after 2 hr. However, the endomorphin-1 liposomes of Examples 14 and 17 prolonged the retention time of the endomorphin-1 in plasma to 24 hr. Also, $T_{1/2}$ was prolonged from 6 min. to 2.4 hr and 1.8 hr, respectively. This result indicates that the stability of the endomorphin-1 in plasma is retained by protection of the liposome.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A delivery system, comprising:
   a carrier having a surface;
   an active compound selected from small molecule compounds or peptides for use as an analgesic encapsulated into the carrier; and
   a glutathione or a glutathione derivative grafted on the surface of the carrier that binds glutathione transporters,
   wherein the glutathione (GSH) or glutathione derivative is covalently bound to polyethylene glycol,
   wherein the polyethylene glycol is covalently bound to vitamin E or a phospholipid, and
   wherein the vitamin E or phospholipid is intercalated into the carrier such that the glutathione or glutathione derivative is grafted on the surface of the carrier that binds glutathione transporters.

2. The delivery system as claimed in claim 1, wherein the carrier comprises a liposome.

3. The delivery system as claimed in claim 2, wherein the liposome comprises at least one of lecithin and hydrogenated lecithin.

4. The delivery system as claimed in claim 3, wherein the liposome further comprises cholesterol, water-soluble vitamin E, or octadecyl amine.

5. The delivery system as claimed in claim 3, wherein lecithin or hydrogenated lecithin has a molar ratio of about 0.5-100%.

6. The delivery system as claimed in claim 4, wherein cholesterol or water-soluble vitamin B has a molar ratio of about 0.005-75%, and octadecyl amine has a molar ratio of about 0.001-25%.

7. The delivery system as claimed in claim 1, wherein the small molecule compounds comprise morphine or gabapentin.

8. The delivery system as claimed in claim 1, wherein the peptides comprise opioid peptides.

9. The delivery system as claimed in claim 8, wherein the peptides comprise enkephalin, endorphin, dynorphin, endomorphin-1 or endomorphin-2.

10. The delivery system as claimed in claim 1, wherein the active compound has a molar ratio of about 0.0005-50%.

11. The delivery system as claimed in claim 1, wherein the carrier has an encapsulation efficiency of about 0.5-100%.

12. The delivery system as claimed in claim 1, wherein the carrier targets glutathione transporters of organs.

13. The delivery system as claimed in claim 1, wherein the carrier targets glutathione transporters of the blood brain barrier.

14. The delivery system as claimed in claim 1, wherein the active compound has a penetration ratio for brain endothelial cells.

15. The delivery system as claimed in claim 14, wherein the cell penetration ratio of the active compound is about 0.01-100%.

16. A method of effecting analgesia, comprising administering the delivery system as claimed in claim 1 to a subject in need thereof.

17. The method of analgesia as claimed in claim 16, wherein the small molecule compounds comprise morphine or gabapentin.

18. The method of analgesia as claimed in claim 16, wherein the peptides comprise opioid peptides.

19. The method of analgesia as claimed in claim 18, wherein the peptides comprise enkephalin, endorphin, dynorphin, endomorphin-1 or endomorphin-2.

20. The method of analgesia as claimed in claim 16, wherein the carrier is a liposome, a nanoparticle, a polymeric micelle or a microsphere.

21. The delivery system as claimed in claim 1, wherein glutathione is grafted on the surface of the carrier.

22. The method of analgesia as claimed in claim 16, wherein glutathione is grafted on the surface of the carrier.

23. A delivery system, comprising:
a carrier; and
glutathione or glutathione derivative,
wherein said carrier is a nanoparticle, a polymeric nanoparticle, a solid liquid nanoparticle, a polymeric micelle, a liposome, microemulsion, or a liquid-based nanoparticle, and
wherein said glutathione or glutathione derivative is covalently bound to polyethylene glycol, wherein the polyethylene glycol is covalently bound to vitamin E or a phospholipid, and wherein the vitamin E or phospholipid is intercalated into the carrier, such that the glutathione or glutathione derivative is on an outside surface of the carrier that binds glutathione transporters.

24. A delivery system, comprising:
a carrier comprising glutathione or a glutathione derivative,
wherein said carrier is selected from group consisting of: a nanoparticle, a polymeric nanoparticle, a solid liquid nanoparticle, a polymeric micelle, a liposome, a microemulsion, and a liquid-based nanoparticle,
wherein said glutathione or glutathione derivative is covalently bound to a polyethylene glycol derivative which is itself covalently bound to a vitamin E derivative or a phospholipid,
wherein said polyethylene glycol derivative is selected from the group consisting of: polyethylene glycol, a polyethylene glycol comprising carboxylic acid, a polyethylene glycol comprising maleimide, a polyethylene glycol comprising an amide, and a polyethylene glycol comprising biotin,
wherein said vitamin E derivative is selected from the group consisting of: vitamin E, α-tocopherol, β-tocopherol, γ-tocopherol, δ-tocopherol, α-tocotrienol, β-tocotrienol, γ-tocotrienol, δ-tocotrienol, α-tocopherol succinate, β-tocopherol succinate, γ-tocopherol succinate, δ-tocopherol succinate, α-tocotrienol succinate, β-tocotrienol succinate, γ-tocotrienol succinate, δ-tocotrienol succinate, α-tocopherol acetate, β-tocopherol acetate, γ-tocopherol acetate, δ-tocopherol acetate, α-tocotrienol acetate, β-tocotrienol acetate, γ-tocotrienol acetate, δ-tocotrienol acetate, α-tocopherol nicotinate, β-tocopherol nicotinate, γ-tocopherol nicotinate, δ-tocopherol nicotinate, α-tocotrienol nicotinate, β-tocotrienol nicotinate, γ-tocotrienol nicotinate, δ-tocotrienol nicotinate, α-tocopherol phosphate, β-tocopherol phosphate, γ-tocopherol phosphate, δ-tocopherol phosphate, α-tocotrienol phosphate, β-tocotrienol phosphate, γ-tocotrienol phosphate, or δ-tocotrienol phosphate, and
wherein the phospholipid has the structure of formula (II):

(II)

wherein $A_2$ is phosphoethanoamine and $R_2$ is selected from the group consisting of: myristoyl, palmitoyl, stearoyl and oleoyl,
wherein the glutathione or glutathione derivative is on an outside surface of the carrier that binds glutathione transporters.

* * * * *